United States Patent [19]

Watanabe

[11] Patent Number: 4,533,457
[45] Date of Patent: Aug. 6, 1985

[54] ION SELECTIVE ELECTRODE DEVICE AND ION ANALYZING APPARATUS

[75] Inventor: Fumio Watanabe, Tokyo, Japan

[73] Assignee: Tokyo Shibaura Denki Kabushiki Kaisha, Kawasaki, Japan

[21] Appl. No.: 524,074

[22] Filed: Aug. 17, 1983

[30] Foreign Application Priority Data

Aug. 28, 1982 [JP] Japan .................. 57-149774

[51] Int. Cl.³ ............................................. G01N 27/46
[52] U.S. Cl. ...................................... 204/411; 204/416
[58] Field of Search .............. 204/416, 417, 418, 419, 204/420, 403, 409, 412, 411, 435; 128/635; 436/52

[56] References Cited

U.S. PATENT DOCUMENTS

| | | | |
|---|---|---|---|
| 3,327,204 | 6/1967 | Hillier et al. | 204/412 X |
| 3,997,420 | 12/1976 | Buzza | 204/420 X |
| 4,053,381 | 10/1977 | Hamblen et al. | 204/416 |
| 4,115,209 | 9/1978 | Freiser et al. | 204/1 T |
| 4,206,027 | 6/1980 | Schindler et al. | 204/412 X |
| 4,233,031 | 11/1980 | Matson et al. | 204/412 X |
| 4,404,065 | 9/1983 | Matson | 204/411 X |

FOREIGN PATENT DOCUMENTS 3010461 10/1981 Fed. Rep. of Germany ...... 204/420

OTHER PUBLICATIONS

Osswald et al., "Flow-Through System of High Stability for Meas. of Ion Activity in Clinical Chem.", Chimia 31 (1977), Nr. 2, (Feb.).

Primary Examiner—G. L. Kaplan
Assistant Examiner—Nam X. Nguyen
Attorney, Agent, or Firm—Cushman, Darby & Cushman

[57] ABSTRACT

An ion selective electrode device is used to electrochemically detect several ion concentrations of an ion-containing liquid. The ion selective electrode device comprises a plurality of ion selective electrodes. These ion selective electrodes each include a substrate of insulating material having a small-diameter through hole, a metal layer formed in one body on an inner peripheral surface of the through hole and both major surfaces of the substrate, and ion sensitive layer formed on the metal layer of the inner peripheral surface. Those ion selective electrodes are connected by insulating plates for maintaining electrical insulation between the adjoining ion selective electrodes in such a manner that these through holes define a flow path for liquid to be examined.

2 Claims, 5 Drawing Figures

F I G. 1
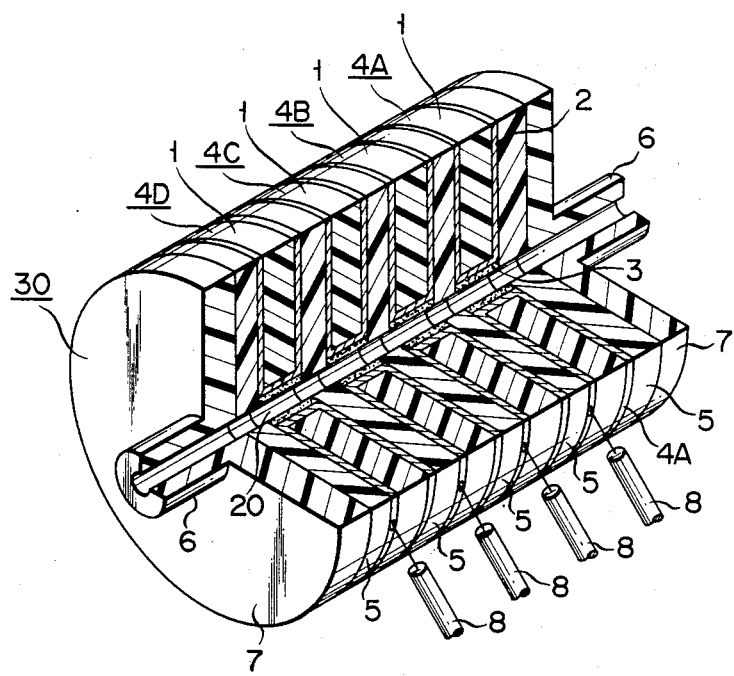

ION SELECTIVE ELECTRODE DEVICE AND ION ANALYZING APPARATUS

BACKGROUND OF THE INVENTION

This invention relates to an ion selective electrode device and a flowthrough type ion analyzing apparatus utilizing the same.

Ion selective electrodes which are combined to constitute an electrode device are generally used to electrochemically detect the concentration of ions of each type contained in sample solution. Various types of ion selective electrodes have been proposed. For example, an ion selective electrode having the following structure is disclosed in Japanese Unexamined (KOKAI) patent application No. 55-154454 (application No. 54-61463). A lead wire for voltage detection is connected to a central portion of an outer surface of a tubular metal substrate having a through hole at its center. Ion sensitive layers are solvent-welded on the inner and outer surfaces of the metal substrate. When a sample solution flows into the through hole to bring ions in the sample solution into contact with the inner ion sensitive layer, a predetermined single electrode potential difference is detected.

In order to independently analyze several types of ion, ion selective electrodes are detachably coupled to each other at predetermined intervals through a connecting tube.

The conventional ion selective electrode of this type and an ion analyzing apparatus using such an ion selective electrode have the following disadvantages.

Since the sample is brought into contact with the metal substrate through the ion sensitive layer, heat dissipation from the sample to the metal substrate is increased, and an ion concentration of the sample cannot be accurately measured (to be described in detail later).

Since a plurality of electrodes are coupled in series with each other through the connecting tube to constitute an electrode device, a concave or stepped portion is formed in a flow path along which the sample flows. As a result, an uniform sample flow is disturbed, resulting in a disadvantage.

Furthermore, since the substrate is made of a metal, precise machining techniques must be employed to form a small-diameter through hole therethrough.

It is a first object of the present invention to provide an ion selective electrode device having a low heat capacity so as to prevent a decrease in temperature of an ion sample while ion concentration is being measured.

It is a second object of the present invention to provide an ion selective electrode device which may be easily manufactured using printed wiring techniques without requiring precise metal working techniques.

It is a third object of the present invention to provide an ion selective electrode device which has no obstacle such as a projection to disturb an uniform sample flow in a flow path for ion measurement.

It is a fourth object of the present invention to provide an ion selective electrode device wherein a plurality of ion selective electrodes are constructed in one body.

It is a fifth object of the present invention to provide an ion analyzing apparatus using such an ion selective electrode device.

SUMMARY OF THE INVENTION

These objects are accomplished in the present invention by providing an ion selective electrode device comprising a plurality of ion selective electrodes which each includes a substrate having a small-diameter through hole that is made of an insulating material, a metal layer formed in one body on an inner peripheral surface of the through hole and both major surfaces of the substrate, and an ion sensitive layer formed at least on the metal layer of said inner peripheral surface, said plurality of ion selective electrodes being connected by insulating members for maintaining electrical insulation between the adjoining ion selective electrodes, whereby said small-diameter through holes define a flow path for a liquid to be examined.

Further these objects are accomplished in the present invention by providing an ion analyzing apparatus comprising an ion selective electrode device having a plurality of ion selective electrodes, and an arithmetic circuit which calculates each concentration of a plurality of ion by processing potential differences derived from said plurality of ion selective electrodes, said plurality of ion selective electrodes including a substrate having a small-diameter through hole that is made of an insulating material, a metal layer formed in one body on an inner peripheral surface of the through hole and both major surfaces of the substrate, and an ion sensitive layer formed at least on the metal layer of said inner peripheral surface, and said plurality of ion selective electrodes being connected by insulating members for maintaining electrical insulation between the adjoining ion selective electrodes, whereby said small-diameter through holes define a flow path for a liquid to be examined.

BRIEF DESCRIPTION OF THE DRAWINGS

FIG. 1 is a partially cut-away perspective view illustrating the construction of the ion selective electrode device according to one preferred embodiment of the present first invention;

DETAILED DESCRIPTION OF THE PREFERRED EMBODIMENTS

Figure 2A:
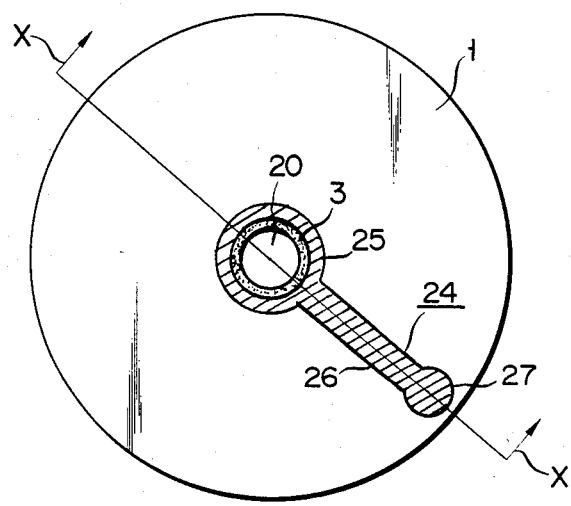
FIG. 2A is a plan view of one side of the ion selective electrode according to another preferred embodiment of the present invention.

Before proceeding with the preferred embodiments, the equation on the single electrode potential (difference) as is known by Nernst's equation will be explained which is relevant to the present invention.

When a metal (electrode) is dipped in an ion conductive solution, a single electrode potential (difference) $E$ is given as follows:

$$E = E_0 + (2.303 RT/nF) \ln a \qquad (1)$$

where $E_0$ is the normal electrode potential (difference) which is an inherent value in a given electrode metal but varies in accordance with a temperature change, $R$ is the gas constant, $n$ is the valence of the ion, $F$ is Faraday's constant, T is the absolute temperature of the sample, and "a" is the activity of the ion.

As will be apparent from equation (1), the ion concentration of the sample has a substantially linear relation with the potential (difference) E when the temperature is kept constant. However, when the temperature changes, the terms $E_0$ and $(2.303RT/nF)\ln a$ change accordingly. As a result, the ion concentration cannot be accurately measured.

An embodiment of an ion selective electrode device according to the first embodiment of the present invention will now be described with reference to FIG. 1.

An ion selective electrode device 30 comprises a plurality of electrodes (e.g., four electrodes 4A, 4B, 4C and 4D in this embodiment), a plurality of disc-shaped insulating plates 5 (e.g., five insulating disc plates in this embodiment) and two holding plates 7. Each of the four electrodes 4A, 4B, 4C and 4D comprises: a disc-shaped substrate 1 made of an insulating material and having a small-diameter hole or through hole 20 (referred to as a "through hole" hereinafter); a metal layer 2 formed on both major surfaces of the disc substrate 1 and on the inner surface defining the through hole 20; and an ion sensitive layer 3 provided on the metal layer 2 formed on the inner surface of the through hole 20. Each of the five insulating disc plates 5 has a through hole of substantially the same diameter as the through hole 20 of each disc substrate 1, and each pair of adjacent plates 5 sandwich one of the four electrodes 4A, 4B, 4C and 4D therebetween. The four electrodes 4A, 4B, 4C and 4D are alternately sandwiched between the five insulating disc plates 5 such that the through holes 20 of the electrodes 4A, 4B, 4C and 4D are aligned with those of the plates 5, and the electrodes 4A, 4B, 4C and 4D and the plates 5 form an integral body. The two holding plates 7 each having a connecting port 6 for the flow path sandwich the resultant integral body therebetween such that the connecting ports 6 of the holding plates 7 are aligned with the integral through hole of the resultant body.

One (e.g., the electrode 4A) of the four electrodes 4A, 4B, 4C and 4D serves as a reference electrode, and the remaining electrodes serve as ion selective electrodes which detect different ions (e.g. $Cl^-$, $K^+$, $Na^+$), respectively.

The disc substrate 1 of each electrode 4A, 4B, 4C or 4D is made of an insulating material and has the through hole 20 having a diameter of about 1 mm. The disc substrate 1 thus has an inner diameter of about 1 mm, an outer diameter of about 10 mm and a thickness of about 1.5 mm. The insulating material used for the disc substrate 1 can be selected from the group consisting of phenolic resins (e.g., Bakelite (registered trademark)), epoxy resins, polyvinyl chloride resins, paper-epoxy mixtures, glass-epoxy mixtures, ceramics, and so on.

The metal layer 2 of each electrode 4A, 4B, 4C or 4D can be formed by adhesion of a metal film, electroless plating, ion plating or deposition, to a thickness of about 10 $\mu$m. In particular, a printed wiring technique used for electronic circuits can be easily utilized for this purpose. A metal for the metal layer 2 can be selected from the group consisting of platinum, gold, copper, etc. The metal layer 2 may be a two-layer structure wherein a first layer of copper is formed on the surface of the disc substrate 1 and a second layer of gold or silver is formed on the first layer. For the electrode which serves as the reference electrode, the surface of the metal layer 2 is preferably coated with at least silver chloride since silver chloride provides chemical stability. Therefore, when silver is used for the metal layer 2 as the reference electrode, silver chloride is precipitated by electrolysis on its surface. However, when a metal such as copper, platinum, or gold (excluding silver) is used for the metal layer 2, it is preferred that the surface of the metal layer 2 is first coated with silver by plating, ion plating or vacuum deposition, and then silver chloride is precipitated by electrolysis on the surface of the silver layer.

The ion sensitive layer 3 of the reference electrode 4A is formed in the following manner to a thickness in the range between 20 $\mu$m and 50 $\mu$m. Twenty-nine weight % of potassium chloride, 7 weight % of polyvinyl chloride and 64 weight % of tetrahydrofuran are mixed to prepare a suspension thereof. This suspension is applied to the surface of the metal layer 2 comprising silver and having silver chloride formed thereon. After the tetrahydrofuran is removed by vaporization, a coating containing potassium chloride is left on the silver chloride film. A solution of polyvinyl chloride and tetrahydrofuran is then applied to the surface of the coating containing potassium chloride, and the tetrahydrofuran is removed by vaporization, thereby forming a polyvinyl chloride film as a protective film.

The ion sensitive layers 3 formed on the respective ion selective electrodes 4B, 4C and 4D are formed as follows.

When the ion selective electrode 4B comprises a chlorine-ion electrode, a solution of 1.8 to 2.3 weight % of methyl tridodecyl ammonium chloride, 6.7 to 7.2 weight % of polyvinyl chloride, and 91 weight % of tetrahydrofuran is applied to the surface of the metal layer 2. Tetrahydrofuran is removed by vaporization, thereby forming a chlorine-ion sensitive layer 3 having a predetermined thickness in the range between, e.g., 20 $\mu$m and 50 $\mu$m.

When the ion selective electrode 4C comprises a potassium-ion electrode, solution of 0.2 to 0.5 weight % of valinomycin, 4.5 to 5.4 weight % of a plasticizer such as dioctyl adipate, 3.7 to 4.5 weight % of polyvinyl chloride, and 89.7 to 91.7 weight % of tetrahydrofuran is applied to the surface of the metal layer 2. Tetrahydrofuran is then removed to leave a potassium-ion sensitive layer 3 having a predetermined thickness in the range between, e.g., 20 $\mu$m and 50 $\mu$m.

When the ion selective electrode 4C comprises a sodium-ion electrode, a solution of 0.2 to 0.5 weight % of monensin, 4.5 to 5.4 weight % of a plasticizer such as dioctyl adipate, 3.7 to 4.5 weight % of polyvinyl chloride, and 89.7 to 91.7 weight % of tetrahydrofuran is applied to the surface of the metal layer 2. Tetrahydrofuran is then removed to leave a sodium-ion sensitive layer 3 having a predetermined thickness in the range between, e.g., 20 $\mu$m and 50 $\mu$m.

The insulating disc plates 5 can be made of the same insulating material as the disc substrates 1 of the electrodes 4A, 4B, 4C and 4D. The insulating disc plates 5 having the same shape as the disc substrates 1 are used to insulate the electrodes 4A, 4B, 4C and 4D from each other.

Referring to FIG. 1, reference numerals 8 denote lead wires. The lead wires 8 are electrically connected by soldering or the like to the metal layers 2 to detect a plurality of the single electrode potential E which is given by equation (1) and is generated by the electrodes 4A, 4B, 4C and 4D, respectively.

When the ion selective electrode device 30 is constructed as described above, the three different ion sensitive layers 3 and the reference electrode 4A are exposed in the flow path defined by the through hole 20. Therefore, when the sample solution flows through the flow path, three types of ions Cl−, K+ and Na+ are simultaneously detected. Although the volume of the flow path defined by the through hole is small and the amount of the sample is very small, piston flow of the sample is realized, thereby precisely detecting the ions. Furthermore, the insulating disc plates 5 and the disc substrates 1, which are made of an insulating material, surround entirely the flow path so that a decrease in temperature of the sample solution upon ion detection can be prevented. Therefore, accurate analysis can be always performed under a predetermined temperature. The function of preventing a temperature decrease cannot be obtained in the conventional case wherein the substrate 1 is made of a metal. Furthermore, the electrodes 4A, 4B, 4C and 4D can be easily manufactured by printed wiring techniques. The present invention thus has an advantage in that the ion selective electrode device 30 can be manufactured at low cost.

Furthermore, the electrodes 4A to 4D, the insulating disc plates 5 and the holding plates 7 are constructed to form one body such that their through holes 20 are aligned with each other. Therefore, no step or obstacle which prevents an uniform flow of the sample solution may be formed in the flow path.

A second embodiment of an ion selective electrode device according to the first invention will be described with reference to FIGS. 2A to 2C.

Only one ion selective electrode is illustrated for the sake of simplicity. The same reference numerals as used in FIG. 1 denote the same parts in FIGS. 2A to 2C.

FIG. 2A is a plan view of one side of a disc substrate 1. The disc substrate 1 has a through hole 20 at substantially the center thereof in the same manner as the disc substrate 1 shown in FIG. 1. An annular portion 25 of an ion selective electrode 24 is formed on a peripheral portion of the through hole 20 in accordance with printed wiring techniques. A terminal portion 27 of the electrode 24 is connected to one end of the annular portion 25 thereof through a bridge portion 26. In other words, the annular portion 25 on one side surface of the electrode 24 is bridged to the terminal portion 27 through the bridge portion 26, thereby obtaining an integral body.

Figure 2B:
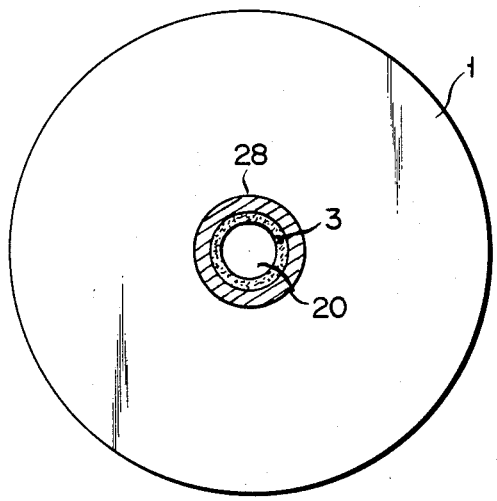
FIG. 2B is a plan view of the opposite side of the ion selective electrode shown in FIG. 2A.

FIG. 2B is a plan view of the opposite side of the ion selective electrode shown in FIG. 2A. Only an annular portion 28 is formed in a peripheral portion of the through hole 20. The reason for this will be described later.

Figure 2C:
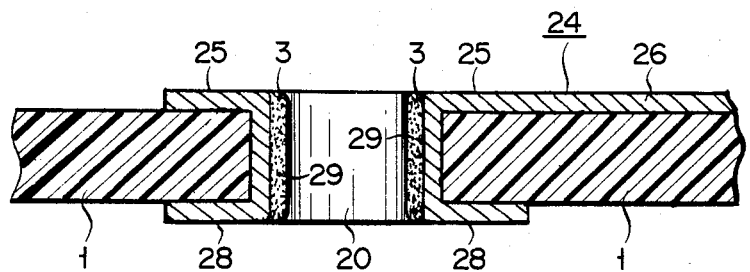
FIG. 2C is an enlarged cross sectional view taken along the line X—X in FIG. 2A.

FIG. 2C is an enlarged cross sectional view taken along the line X—X in FIG. 2A.

As will be apparent from FIG. 2C, the annular portion 25 and the annular portion 28 of the electrode 24 formed on respective side surfaces of the disc substrate 1 are connected to each other through a bridge portion 29 formed on the inner wall of the through hole 20. Thus, the electrode 24 is constructed as one body comprising the annular portions 25 and 28, the bridge portions 26 and 29, and a terminal portion 27 for a lead wire, in accordance with printed wiring techniques.

Similarly, an ion sensitive layer 3 is formed on the outer surface of the bridge portion 29 of the through hole 20. The sample solution flows along the surface of the layer 3.

The surface area (and hence heat capacity) of the metal electrode 24 having the above construction can be considerably decreased, compared to that of the electrode shown in FIG. 1. A decrease in sample temperature can thus be further prevented as compared to the case of the first embodiment.

As is apparent from the first and second embodiments, the electrodes 4A to 4D and the electrode 24 are respectively adhered to each other through the insulating plates 5, thus completely preventing the sample from flowing into a space between, for example, the electrode 4B and the corresponding insulating plate 5 to short-circuit the electrode 4B with the adjacent electrode 4A or 4C.

A flowthrough type ion analyzing apparatus according to the first preferred embodiment of the present second invention will now be described.

Figure 3:
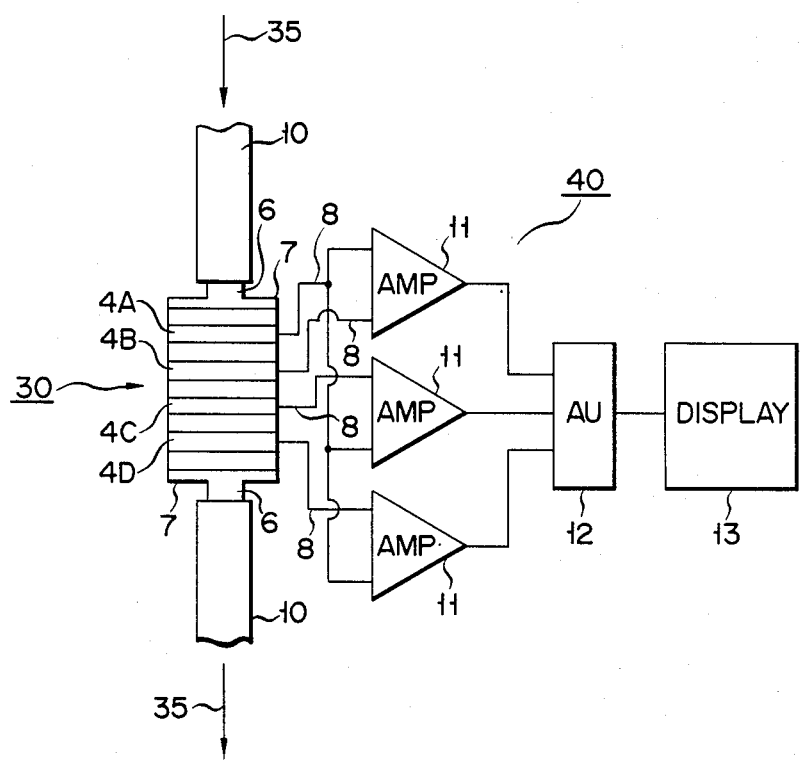
FIG. 3 shows a schematic diagram of the ion analyzing apparatus according to one preferred embodiment of the present second invention.

Referring to FIG. 3, reference numeral 40 denotes an ion analyzing apparatus in accordance with another feature of the present invention. The ion analyzing apparatus 40 has the ion selective electrode device 30 shown in FIG. 1. Tubes 10 are connected to the connecting ports 6 for the flow path of the holding plates 7 at the both ends of the ion selective electrode device 30. A sample solution such as serum (not shown) flows in a direction indicated by an arrow 35. Reference numerals 11 denote amplifiers. The amplifiers 11 amplify the three potential differences of the electrodes 4B, 4C and 4D with respect to that of the fourth electrode 4A of the ion selective electrode device 30. More particularly, the amplifiers 11 amplify to the desired value, the single electrode potential differences E appearing at each of the electrodes 4B, 4C and 4D, with respect to the reference electrode 4A as the common electrode. In general, the single electrode potential E is low. For example, a single electrode potential for the potassium ions is 59.15 mV (25° C.). Reference numeral 12 denotes an arithmetic circuit. The three single electrode potential differences appearing at the electrodes 4B, 4C and 4D with respect to the reference electrode 4A are processed by the arithmetic circuit 12 in accordance with a time division system. The arithmetic circuit 12 uses equation (1) as previously explained to calculate the various ion concentrations in the sample solution in accordance with the time division method. Reference numeral 13 denotes a display device for displaying the concentrations of the various types of ions calculated by the arithmetic circuit 12.

In the flowthrough type ion analyzing apparatus 40, having the above construction, when a serum sample flows in the direction indicated by the arrow 35 in FIG. 3 and the serum sample flows through the ion selective electrode device 30, the potentials corresponding to the ions Cl−, K+ and Na+ in the serum sample are generated at the electrodes 4B, 4C and 4D with respect to the reference electrode 4A. These potentials are applied to the amplifiers 11 through the corresponding lead wires 8. The potentials are then amplified by the corresponding amplifiers 11, so that the amplified potentials are applied to the arithmetic circuit 12. The arithmetic circuit 12 calculates the concentration of Cl−, K+ and Na+ ions in accordance with the potentials at the electrodes 4B, 4C and 4D with respect to the reference electrode 4A. The calculated results are then displayed at the display device 13.

When the flowthrough type ion analyzing apparatus 40 using the ion selective electrode device 30 shown in FIG. 1 is constructed as described above, and only a small amount of sample solution flows therethrough, concentrations of several types of ions can be accurately calculated and displayed.

While the present invention has been described in terms of certain specific embodiments, those skilled in the art will readily appreciate that various modifications, changes, omissions and substitutions may be made without departing from the technical scope and the spirit of the invention.

In the above embodiments of the ion selective electrode device, the ion selective electrode device has four electrodes including a reference electrode. However, the ion selective electrode device may have at least five electrodes including an electrode for detecting any ion other than $Cl^-$, $K^+$ and $Na^+$ ions. Furthermore, in addition to the electrodes for detecting ions, a temperature compensation electrode for detecting the temperature of the flowing sample solution may be included in the ion selective electrode device. For example, a thermistor, a platinum resistor, a metal oxide resistor (e.g., platinum oxide), a thermocouple, a semiconductor temperature sensor or the like may be used as the temperature compensation electrode as needed.

In the above embodiment of the flowthrough type ion analyzing apparatus, an ion selective electrode device having such a temperature compensation electrode may be used to detect the temperature of the sample solution by means of a potential generated by the temperature compensation electrode. In this case, a flowthrough type ion analyzing apparatus may be constructed such that an arithmetic circuit calculates the ion concentration according to the equation (1) under the detected temperature with respect to that under a preset temperature.

Furthermore, regarding the ion selective electrode, the through hole need not be formed substantially at the center of the disc substrate, but may be formed at another position thereof. In the first embodiment, one through hole is formed in the disc substrate. However, a plurality of through holes may be formed in the substrate (for example, the electrode construction in FIG. 2 can be utilized). In this case, several types of ions can be precisely and simultaneously detected.

The shape of the disc substrate and the insulating plate is not limited to a disc shape, but may be extended to any shape. Furthermore, since the substrate and the insulating plate are made of an insulating material, they can have a complex shape.

What is claimed is:

1. An apparatus for detecting the concentration of ions in a solution, comprising:
   at least one reference electrode and one ion selective electrode which are fabricated in the substantially same construction, and which each includes:
   a substrate of an electrically insulating material defining a first small-diameter through hole bounded by an inner peripheral surface of said substrate,
   an electrically conductive layer disposed on said substrate to cover the entire inner peripheral surface of said substrate bounding said first through hole and at least a part of another surface of said substrate different from said inner peripheral surface, and
   an ion selective layer formed at least on the electrically conductive layer disposed on said entire inner peripheral surface of said substrate;
   a plurality of electrically insulating members each defining a second small-diameter through hole, one of said insulating members disposed between each of said reference and ion selective electrodes to form a stack, wherein said first and second small-diameter through holes are in mutual registration to define a straight flow passage through said stack; and
   means for defining an inlet at one end of said passage adapted to receive said solution and an outlet at the other end of said passage adapted to exhaust said solution,
   wherein said ion selective layers formed over the inner peripheral surface of said substrates of said reference and ion selective electrodes are the only portions of said reference and said ion selective electrodes which directly contact said solution flowing through said flow passage, wherein said electrically conductive layer comprises at least first and second annular portions, a bridge portion and a terminal portion, said terminal portion being electrically connected via said bridge portion to one of said first and second annular portions whereby potential differences produced between said ion selective layers of said reference and ion selective electrodes are conducted to said terminal portion.

2. An apparatus for measuring the ion concentration of a solution, comprising:
   reference electrode means for producing a first electrical potential, said reference electrode means including:
   means for thermally insulating said solution, said thermal insulating means including means for defining a first aperture;
   first ion sensitive layer means, disposed on the periphery of said first aperture, for producing said first electrical potential; and
   first electrical conducting means, disposed on said thermal insulating means in contact with said first layer means, for conducting said first electrical potential;
   at least one ion selective electrode means for producing a second electrical potential, said ion selective electrode means including:
   means for thermally insulating said solution, said thermal insulating means including means for defining a second aperture;
   second ion sensitive layer means, disposed on the periphery of said second aperture, for producing said second electrical potential; and
   second electrical conducting means, disposed on said thermal insulating means in contact with said second layer means, for conducting said second electrical potential;
   means for attaching said reference electrode means and said ion selective electrode means together in a stack such that said first and second apertures are in registry;
   means, coupled to said first and second apertures, for inducing a flow of said solution through said first and second apertures; and
   means, connected to receive said first and second electrical potentials conducted by said first and second electrical conducting means, for converting the difference between said first and second electrical potentials to indicia of ion concentration, wherein:
   said thermal insulating means of said ion selective electrode means comprises a disk having first and second opposing flat surfaces, said second aperture being defined in the substantial center of and axially through said disk; and said second electrical conducting means comprises:

a first annular portion disposed on the first surface of said disk surrounding said second aperture;

a second annular portion disposed on the second surface of said disk surrounding said second aperture;

a third annular portion, disposed within said second aperture on the inner peripheral surface of said disk defining said second aperture, said third portion electrically connecting said first and second annular portions, and second ion sensitive layer means disposed on said third annular portion; and terminal means, disposed on said first surface of said disk, for electrically connecting said first annular portion of said converting means.

* * * * *